(12) United States Patent
Demirjian

(10) Patent No.: US 11,458,215 B1
(45) Date of Patent: Oct. 4, 2022

(54) WEARABLE SANITIZING DISPENSER

(71) Applicant: Greg Demirjian, Fairfax Station, VA (US)

(72) Inventor: Greg Demirjian, Fairfax Station, VA (US)

( * ) Notice: Subject to any disclaimer, the term of this patent is extended or adjusted under 35 U.S.C. 154(b) by 1 day.

(21) Appl. No.: 17/322,535

(22) Filed: May 17, 2021

Related U.S. Application Data

(60) Provisional application No. 63/026,085, filed on May 17, 2020.

(51) Int. Cl.
| | | |
|---|---|---|
| *A61L 2/00* | (2006.01) | |
| *A45F 5/00* | (2006.01) | |
| *A44C 5/18* | (2006.01) | |
| *A47K 5/12* | (2006.01) | |
| *A61L 2/26* | (2006.01) | |

(52) U.S. Cl.
CPC ............. *A61L 2/0088* (2013.01); *A44C 5/18* (2013.01); *A45F 5/00* (2013.01); *A47K 5/1201* (2013.01); *A47K 5/1211* (2013.01); *A61L 2/26* (2013.01); *A45F 2005/008* (2013.01); *A61L 2202/15* (2013.01); *A61L 2202/16* (2013.01)

(58) Field of Classification Search
CPC ...... A61L 2/0088; A61L 2/16; A61L 2202/15; A61L 2202/16; A44C 5/18; A45F 5/00; A45F 2005/008; A47K 5/00; A47K 5/1201; A47K 5/1211
See application file for complete search history.

(56) References Cited

U.S. PATENT DOCUMENTS

| | | | | |
|---|---|---|---|---|
| 5,924,601 | A * | 7/1999 | Chen ......................... | F41H 9/10 |
| | | | | 222/78 |
| 7,316,332 | B2 * | 1/2008 | Powers ............... | A61M 35/003 |
| | | | | 222/491 |
| 9,238,539 | B2 * | 1/2016 | Lynch ....................... | A45F 5/00 |
| 9,347,749 | B2 * | 5/2016 | Olah ......................... | F41H 9/10 |
| 9,578,935 | B2 * | 2/2017 | Horgan ................. | A45D 34/00 |
| 9,888,816 | B1 * | 2/2018 | Shaukat ............... | A44C 5/0007 |
| 10,264,859 | B2 * | 4/2019 | Parker ...................... | A61L 2/18 |
| 11,298,712 | B2 * | 4/2022 | Swain ................. | B05B 11/3073 |
| 2004/0162534 | A1 * | 8/2004 | Powers .................. | A47K 5/122 |
| | | | | 604/310 |
| 2008/0230560 | A1 * | 9/2008 | Powers .................. | A45D 34/00 |
| | | | | 264/250 |
| 2011/0155765 | A1 * | 6/2011 | Properzi .............. | A47K 5/1201 |
| | | | | 222/401 |

(Continued)

*Primary Examiner* — Vishal Pancholi
(74) *Attorney, Agent, or Firm* — Neo IP

(57) ABSTRACT

A device for wearing on a person's wrist and dispensing a liquid, such as sanitizing liquid, includes a wristband that has a central mount and two opposing ends. Each end has one part of a two-part mechanical fastener. A container is fixed with the central mount of the wristband and has a top side, a side wall, and a bottom side. The side wall includes an open portion that is fixed with a nozzle. The top side includes a resilient pump diaphragm. The top side, side wall, and bottom side all define an internal volume within the container. Preferably the bottom side of the container includes a removable cap that is removable form the container to provide access to the internal space for refilling the container with the liquid. Depressing the pump diaphragm forces the liquid to be dispensed out of the nozzle.

16 Claims, 5 Drawing Sheets

(56) References Cited

U.S. PATENT DOCUMENTS

| | | | | |
|---|---|---|---|---|
| 2015/0158042 A1* | 6/2015 | Parker | .................. | A44C 15/005 |
| | | | | 222/183 |
| 2016/0044997 A1* | 2/2016 | Horgan | ............... | A61M 35/003 |
| | | | | 222/175 |
| 2017/0156454 A1* | 6/2017 | Abadi | .................. | A47K 5/1201 |
| 2020/0245822 A1* | 8/2020 | Chacon, Jr. | ............ | G04G 17/08 |

* cited by examiner

US 11,458,215 B1

WEARABLE SANITIZING DISPENSER

CROSS-REFERENCE TO RELATED APPLICATIONS

This application claims the benefit of U.S. Provisional Patent Application 63/026,085, filed on May 17, 2020, and is incorporated herein by reference.

STATEMENT REGARDING FEDERALLY SPONSORED RESEARCH AND DEVELOPMENT

Not Applicable.

FIELD OF THE INVENTION

This invention relates to dispensers, and more particularly to a wearable dispenser for sanitizing fluid.

BACKGROUND

With the advent of the COVID 19 pandemic, being able to sanitize one's hands more frequently is desired. Having a container with sanitizing fluid handy is helpful in this regard, as is having a container with other liquids such as sunscreen lotion, hand soap, or the like. Yet often containers, even if small, are inconvenient to carry and use.

Therefore, there is a need for a device that can dispense a liquid from a container that is easily attached with a person. Such a needed invention would allow the user to wear the container on his wrist in an attractive manner. Dispensing the liquid into the user's hand would be easy and intuitive. Further, such a needed device could be attachable to other items such as a wall hanging bracket, or the like. The present invention accomplishes these objectives.

SUMMARY OF THE INVENTION

The present device is for wearing on a wrist of a person and dispensing a liquid. The liquid may be a sanitizing liquid, soap, sunscreen lotion, cologne, or the like.

The device includes a wristband that has a central mount and two opposing ends. Each end has one part of a two-part mechanical fastener, such as a belt and buckle arrangement. A container is fixed with the central mount of the wristband and has a top side, a side wall, and a bottom side. Preferably the side wall takes the shape of the central mount of the wristband for slidable engagement selectively therein. The side wall includes an open portion that is fixed with a nozzle. The top side includes a resilient pump diaphragm. The top side, side wall, and bottom side all define an internal volume within the container. resilient pump diaphragm is preferably made with a low density polyethylene, such that depressing the resilient pump diaphragm reduces the internal volume within the container to force the liquid through the nozzle.

In use, the person secures the wristband around his wrist, such as his left wrist, whereby with his right thumb he can depress the resilient pump diaphragm with his thumb to dispense the liquid out of the nozzle into his hand, or with his fingers around the far side of his left wrist he can depress the resilient pump diaphragm to dispense the liquid out of the nozzle into his hand. Alternate hands may be used for those who are left handed or those who prefer to wear the device on their right wrist.

Preferably the bottom side of the container includes a removable cap that is removable from the container to provide access to the internal space for refilling the container with the liquid. In such an embodiment, preferably the removable cap has a resilient annular seal with the side wall of the container that can be overcome by manual pressure. Alternately, the removable cap includes screw threads that engage cooperative screw threads of the side wall of the container, such that the removable cap can be selectively screwed to or unscrewed from the container. Preferably the removable cap, or the top side of the container is at least partially transparent, such that a level or amount of the liquid in the container is visually ascertainable.

Preferably the container is removably attached with the central mount of the wristband. As such, with the removable cap removed from the container, the container is free to slide out of the central mount of the wristband. The central mount of the wristband preferably includes an opening cooperative with the nozzle of the container to allow the liquid to be dispensed through the opening of the wristband. Preferably the container and the central mount are cooperatively keyed such that the container only fits into the central mount of the wristband in one orientation, wherein the nozzle is aligned with the opening in the wristband.

The present device can dispense a liquid from a container that is easily attached with a person, such as with a wristband on his wrist. The present invention allows the user to wear the container on his wrist, and to dispense the liquid into the user's hand easily and intuitively. Further, the present invention is attachable to other items, such as a wall hanging bracket, or the like. Other features and advantages of the present invention will become apparent from the following more detailed description, taken in conjunction with the accompanying drawings, which illustrate, by way of example, the principles of the invention.

DETAILED DESCRIPTION OF THE PREFERRED EMBODIMENT

Illustrative embodiments of the invention are described below. The following explanation provides specific details for a thorough understanding of and enabling description for these embodiments. One skilled in the art will understand that the invention may be practiced without such details. In other instances, well-known structures and functions have not been shown or described in detail to avoid unnecessarily obscuring the description of the embodiments.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively. Additionally, the words "herein," "above," "below" and words of similar import, when used in this application, shall refer to this application as a whole and not to any particular portions of this application. When the claims use the word "or" in reference to a list of two or more items, that word covers all of the following interpretations of the word: any of the items in the list, all of the items in the list and any combination of the items in the list. When the word "each" is used to refer to an element that was previously introduced as being at least one in number, the word "each" does not necessarily imply a plurality of the elements, but can also mean a singular element.

Figure 1:
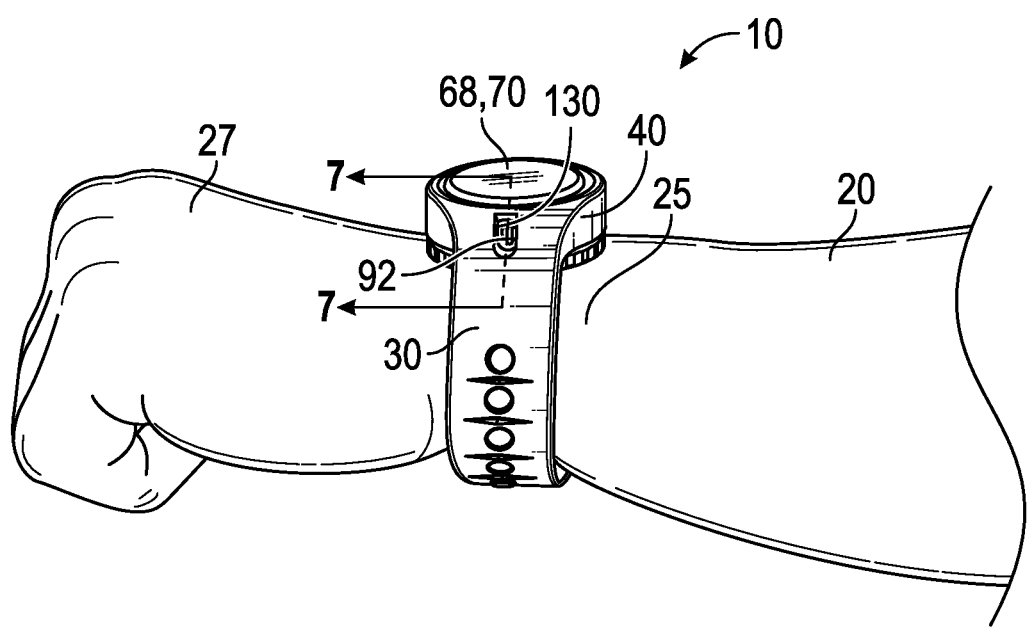
FIG. 1 is a perspective view of the invention, illustrating a wristband with a container for a liquid as affixed with a person's wrist.
Figure 2:
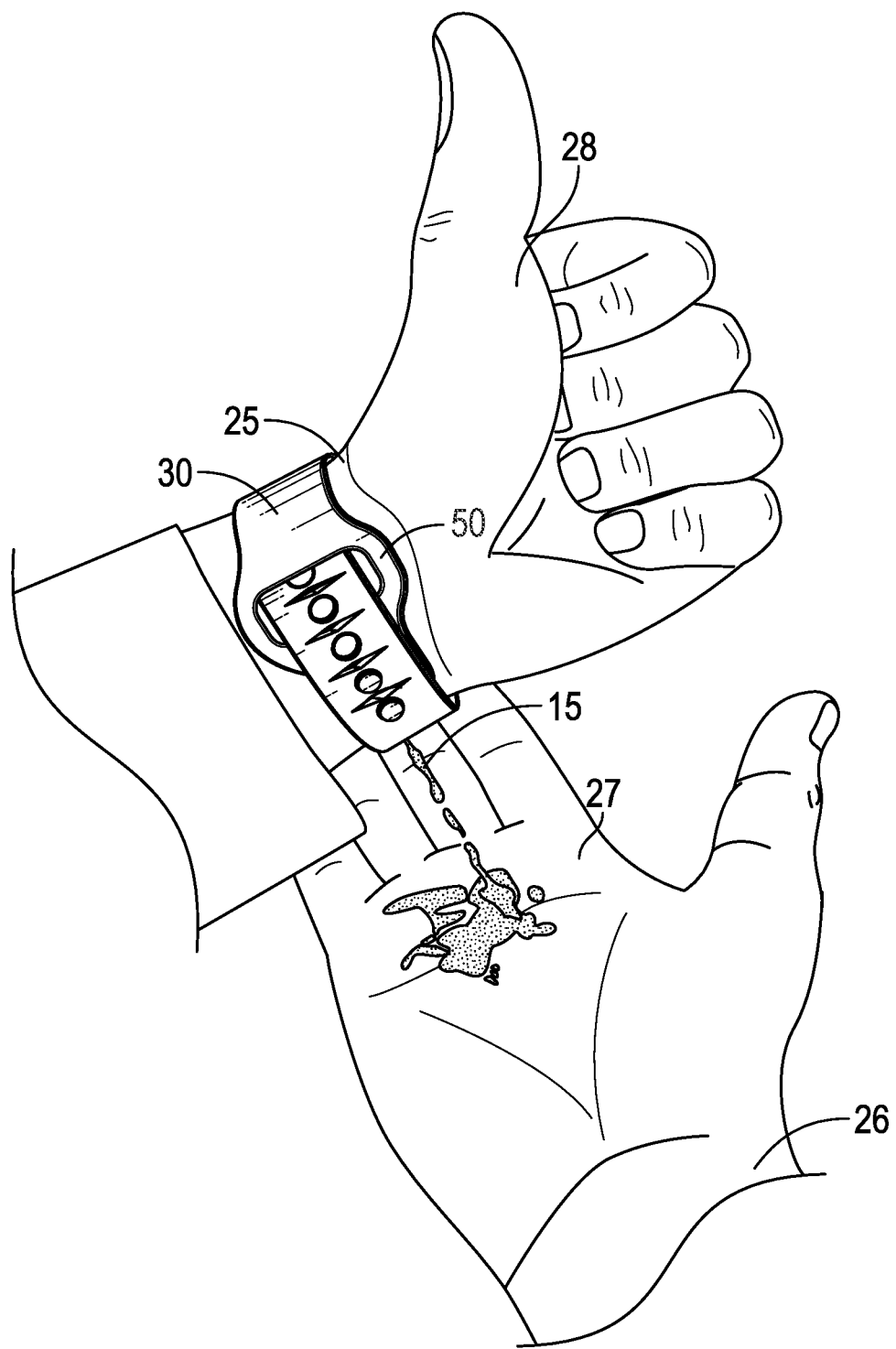
FIG. 2 is a perspective view of the invention, illustrating the liquid being dispensed into the person's hand.

FIGS. 1 and 2 illustrate a device 10 for wearing on a wrist 25 of a person 20 and dispensing a liquid 15. The liquid 15 may be a sanitizing liquid, soap, sunscreen lotion or gel, cologne, or the like. The device 10 is attractive and aesthetically pleasing, and can be made in any number of different styles, shapes, and colors, with a wide variety of applied designs such as sports figures, teams, brands, artwork, graphics, or the like.

The device 10 includes a wristband 30 that has a central mount 40 and two opposing ends 35. Each end 35 has one part 51,52 of a two-part mechanical fastener 50, such as a belt and buckle arrangement (as illustrated), a mechanical snap arrangement (not shown), a hook-and-loop type fastener arrangement (not shown), or the like. Preferably the central mount 40 takes the shape of a ring, but can also be formed as a square, rectangle, hexagon, or other suitable shape. The wristband 30 may be made from a resilient rubber material, plastic, fabric, leather, or the like.

A container 60 is fixed with the central mount 40 of the wristband 30 and has a top side 68, a side wall 65, and a bottom side 62. Preferably the side wall 65 takes the shape of the central mount 40 of the wristband 30 for slidable engagement selectively therein. The side wall 65 includes an open portion 80 that is fixed with a nozzle 90. The top side 68 includes a resilient pump diaphragm 70, preferably made with a low density polyethylene (LDPE) or similar material. The top side 68, side wall 65, and bottom side 62 all define an internal volume 100 within the container 60. A resilient pump diaphragm 70 is preferably made with a low density polyethylene, or similar material, such that depressing the resilient pump diaphragm 70 reduces the internal volume 100 within the container 60 to force the liquid 15 through the nozzle 90. The container 60 is preferably made from a transparent or translucent injection-molded plastic material, such as low-density polyethylene, PET, or the like.

Figure 5:
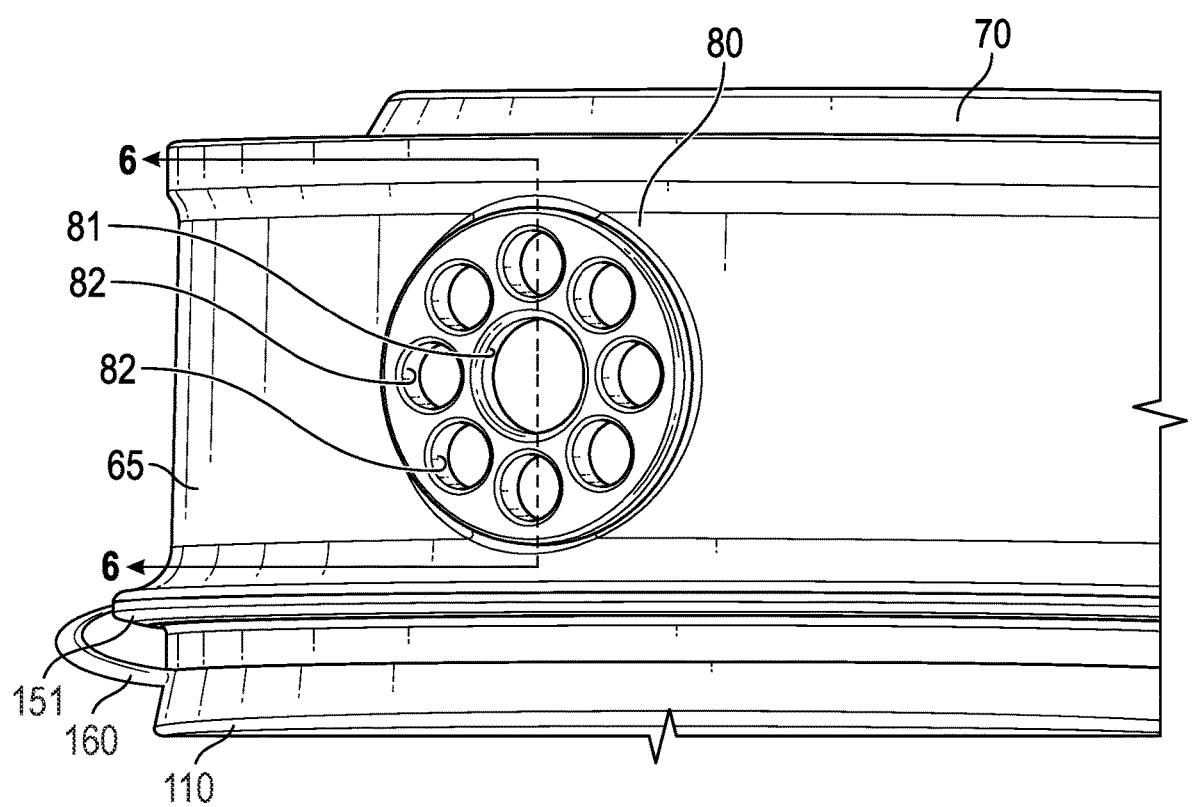
FIG. 5 is an enlarged view of an open portion of the side wall of the container, a nozzle and an umbrella valve of the invention omitted for clarity of illustration.
Figure 6:
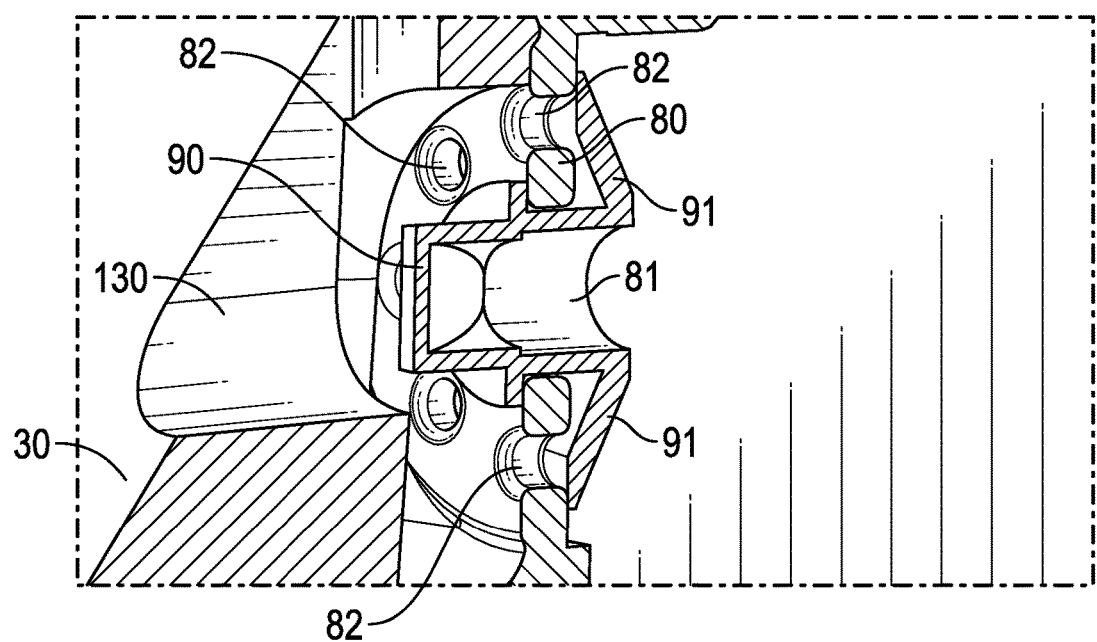
FIG. 6 is a cross-sectional view across the nozzle and umbrella valve as affixed with the open portion of the side wall of the container, taken generally along lines 6-6 of FIG. 5.

The nozzle 90 preferably includes a dual duck-bill umbrella valve 91 (FIG. 6), and the open portion 80 of the side wall 65 of the container 60 preferably includes a central aperture 81 (FIG. 5) through which the nozzle 90 projects. The open portion 80 further includes a plurality of air apertures 82 through which air re-enters the internal volume 90 when the resilient pump diaphragm 70 returns to a normal position after being depressed to expel the liquid 15, air being drawn in through the air apertures 82 and slightly deforming the umbrella valve 91 to allow air to enter the internal volume 100 in place of the liquid 15 that was expelled. The umbrella valve 91 then seals the air apertures 82 once the internal volume 100 returns to ambient pressure.

The umbrella valve 91 and nozzle 90 are preferably integrally formed from an elastomeric rubber material, such as silicone rubber or the like.

Preferably the nozzle 90 is normally closed when the resilient pump diaphragm 70 is not depressed, but under pressure when the resilient pump diaphragm 70 is depressed, the nozzle 90 opens to allow dispensing of the liquid 15 there through, given enough pressure to overcome the resilient force of the nozzle 90 to remain closed.

In use, with the fluid 15 in the container 60, the person 20 secures the wristband 30 around his wrist 25, such as his left wrist 25 (FIG. 1), whereby with his right thumb he can depress the resilient pump diaphragm 70 with his thumb to dispense the liquid 15 out of the nozzle 90 into his hand 27 (FIG. 2), or with his fingers around the far side of his left wrist 25 he can depress the resilient pump diaphragm 70 to dispense the liquid 15 out of the nozzle 90 into his hand 27. Alternate hands 27,28 may be used for those who are left handed or those who prefer to wear the device 10 on their right wrist 26.

Figure 3:
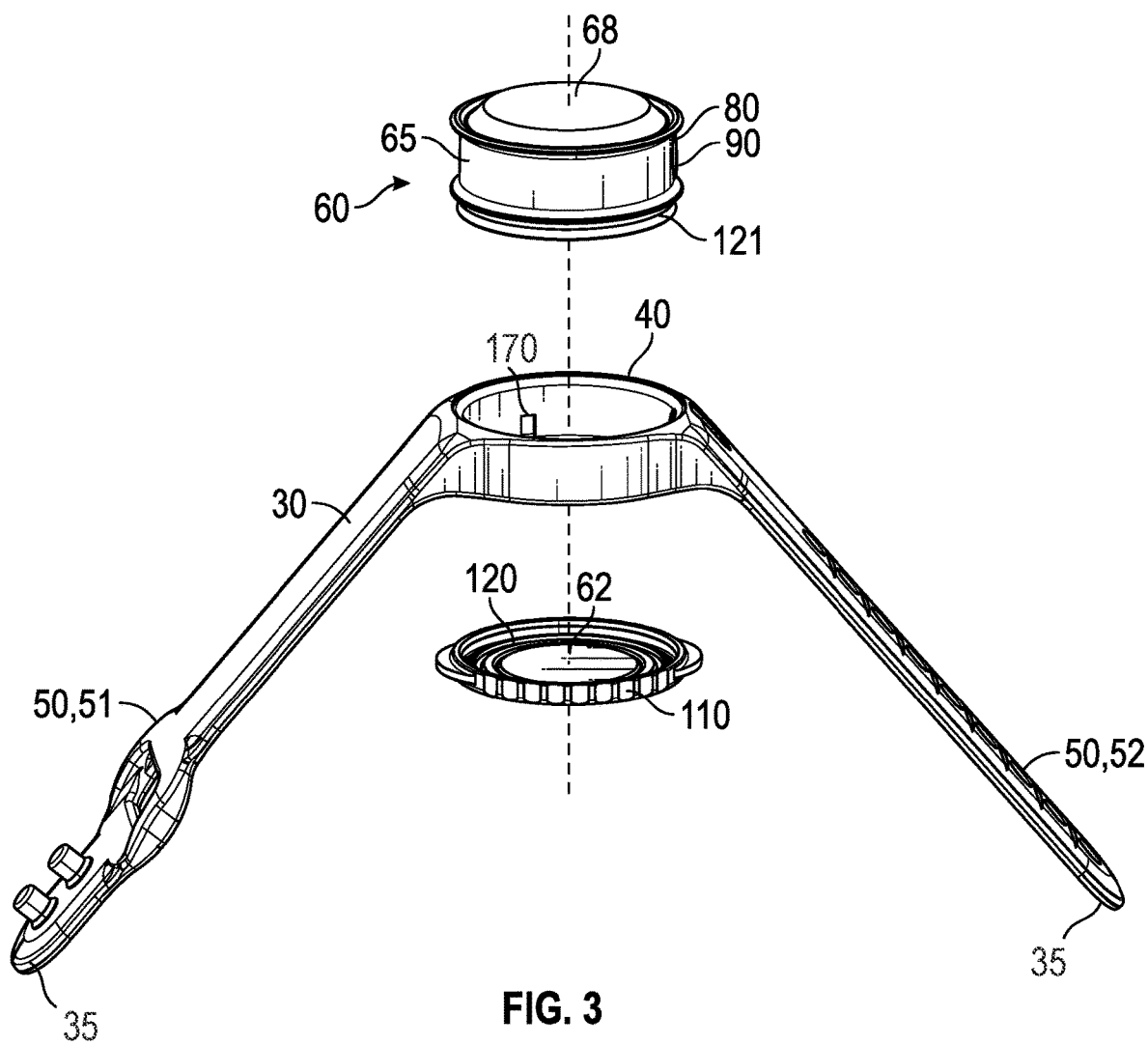
FIG. 3 is an exploded perspective view of the invention.
Figure 7:
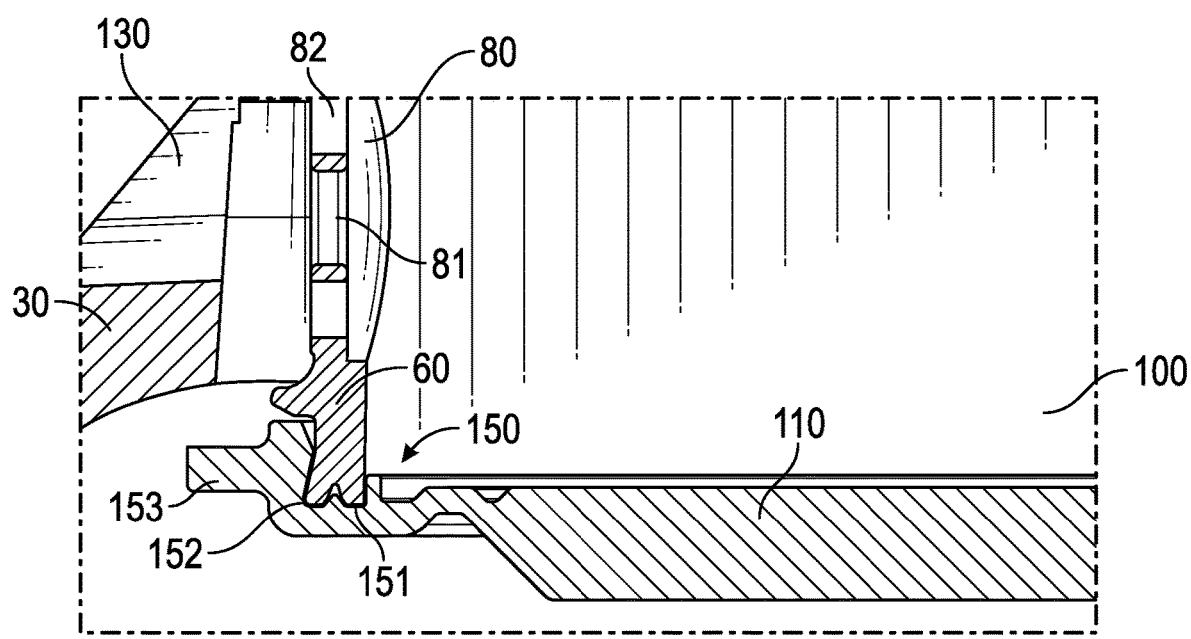
FIG. 7 is an enlarged cross-sectional view of an annular seal of a removable cap with the container, taken generally along lines 7-7 of FIG. 1.

Preferably the bottom side 62 of the container 60 includes a removable cap 110 (FIG. 3) that is detachable from the container 60 to provide access to the internal space 100 for refilling the container 60 with the liquid 15. In such an embodiment, the removable cap 110 preferably includes an annular seal 150 (FIG. 7) that is formed between a V-shaped rim 151 of the side wall 65 of the container 60 and a receiver 152 of the removable cap 110. The receiver 152 deforms slightly as the rim 151 of the side wall 65 is pressed into the receiver 152, creating a resilient friction fit that is water tight. The removable cap 110 may include a tab 153 for aiding the person 20 in prying off the removable cap 110 from the container 60. Further, the removable cap 110 may be affixed with a tether or living hinge 160 to the rim 151 of the container 60 so that the cap 110 is not misplaced. In such an embodiment the container 60, living hinge 160, and removable cap 110 may be all integrally formed with the same elastomeric material.

Alternately, the removable cap 110 includes screw threads 120 (FIG. 3) that engage cooperative screw threads 121 of the side wall 65 of the container 60, such that the removable cap 110 can be selectively screwed to or unscrewed from the container 60. Preferably the removable cap 110, or the top side 68 of the container 60 is at least partially transparent, such that a level or amount of the liquid 15 in the container 60 is visually ascertainable.

Preferably the container 60 is removably attached with the central mount 40 of the wristband 30. As such, with the removable cap 110 removed from the container 60, the container 60 is free to slide out of the central mount 40 of the wristband 30. The central mount 40 of the wristband 30 preferably includes an opening 130 (FIG. 1) cooperative with the nozzle 90 of the container 60 to allow the liquid 15 to be dispensed through the opening 130 of the wristband 130. Preferably the container 60 and the central mount 40 are cooperatively keyed with a notch 170 in the central mount 40 (FIG. 3) and a corresponding protrusion on the container 60 (not shown) such that the container 60 only fits into the central mount 40 of the wristband 30 in one orientation and is prevented from rotating, wherein the nozzle 90 is aligned with the opening 130 in the wristband 30.

Figure 4:
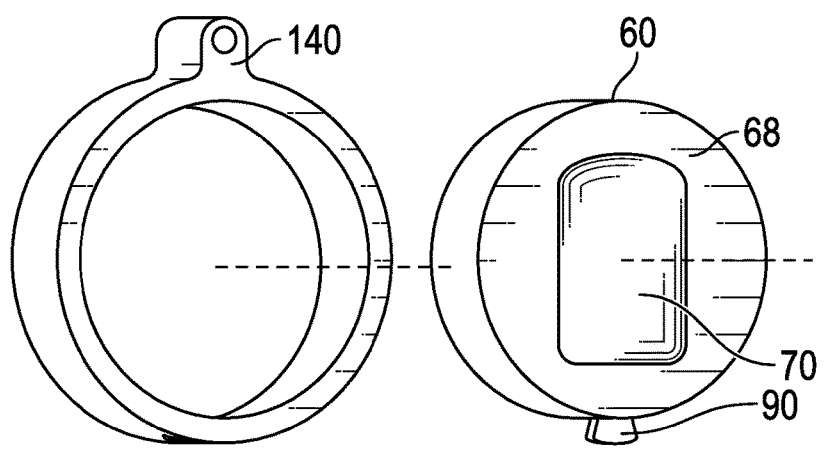
FIG. 4 is an exploded perspective view of an alternate embodiment of the invention.

An auxiliary container mount 140 may be included for accepting the container 60 therein when the container 60 is removed from the wristband 30. Such an auxiliary container mount 140 may be, for example, a wall bracket (FIG. 4), a cell phone case (not shown), a key ring (not shown), a pendant receiver for a necklace (not shown), or the like. Further, additional features may be added to the device 10, such as an RFID tag for using the device 10 as an ID bracelet, for example.

The so-called "WearSpray" invention of the present application is an innovative, wearable, fluid dispensing apparatus device. Aesthetically pleasing and stylish, WearSpray offers the ability to quickly dispense a fluid from a reservoir through a dual purpose, two-way valve. The air-tight reservoir can contain fluids to dispense, such as sanitizers, sunscreens, insect repellants, perfumes, lotions, medications and other liquids that make the device appealing to those individuals who require an application of a fluid, lotion or solution quickly.

Previous dispensing devices of prior art often have springs, pumps, levers, gears, batteries or pressurized cartridges. Advantageously, the WearSpray invention overcomes the shortcomings of this prior art with three perfectly designed components that work seamlessly together. A reservoir, a dual purpose valve and an airtight cap are the three main components of a WearSpray device.

Working together, the fluid that is discharged from a WearSpray reservoir and valve can stream eight feet through the air once dispensed from the valve. Air is sucked back in through the umbrella side of the valve, to repurpose the apparatus. The airtight cap, that allows WearSpray to be easily refilled with no secondary devices, snaps in place as an "Annular Seal" to hold over 90 streams in the refillable reservoir.

The WearSpray device has many uses, these include being worn on the wrist, as a pendant, as a keychain, attached to the back of a cell phone, or the like. The WearSpray apparatus can also be placed on the wall for easy dispensing using its three main components of various sizes. Other possible embodiments can also be in situation where a small device is needed to clean a part or surface.

As the world is becoming more technologically advanced, companies find it necessary to have transactions with touch-less technology such as an RFID chip. WearSpray Clean Bands can also have the option to be made with a built-in re-writable Radio Frequency Identification (RFID) chip. This added feature is recommended for specific industries such as retail, military, hotel, and entertainment sectors, that may require increased safety and security, touch-less transactions, locks, and access points, tracking and enhanced guest experiences across a multitude of environments.

All of the aforementioned characteristics is what makes WearSpray Clean Bands a unique and extraordinary wearable sanitizer device.

Challenges

There were many challenges in creating this wearable, stylish, dynamic dispenser. It had to be created with injection molded parts that be easily replicated with quality materials. It had to look stylish on someone's wrist and work effortlessly with a large refillable area so that no secondary device was needed to refill it. It needed to be built with as few working parts as possible to create the ease of replication, cost, and assembly.

The analogous fluid, or contents within the reservoir, are visibly detected through the transparent dispenser.

Anyone can put a spray bottle attached to your wrist or a bottle attached to your wrist to inject a fluid, but will it look good and how is it refilled and how can it be replicated?

All these main issues and challenges of the design and creation of WearSpray were slowly overcome with solutions.

Process of Engineering

Initially, the design and manufacturing process were too perplexing and complicated to understand.

After engineering testing and re-design, this small, yet powerful device was designed to be built with injected molded parts. Injection molded parts have manufacturing boundaries that need to be specifically addressed, or you will not succeed in developing your components. This is the science of injection molded parts being designed for manufacturing or "DFM." There are boundaries and nuances to consider through the entire process of building molds and using quality materials that create a quality device.

The Reservoir

The reservoir, created in the shape of a diaphragm, was specifically designed in such a way that when pushed, pressure would discharge the liquid through the middle wall holding the valve in a specifically designed gate for the size of the reservoir. As air and liquid escapes, it thereby creates a vacuum, where air would then be "sucked back" in through the sides of the dual purpose Duckbill/Umbrella valve. In other prior art devices, this pressure has often been created with various springs, levers or replaceable pressurized containers. WearSpray overcame this design with its airtight, flexible reservoir.

Reservoir Material

The low density polyethylene (LDPE) materials that are used in the injection molded parts are transparent and have been built this way so that the person or wearer of the device can view or see directly into the reservoir to understand how much solution liquid or cream they have left. Additionally, the transparency of the material has a dual purpose; to allow visibility to the user of the quantity of solution in the reservoir, and to feature the beauty of light passing through the reservoir, to highlight the sleek modern design.

The Low-density polyethylene material (LDPE) was specially chosen to hold fluid that could contain corrosive alcohol and would not destroy the material.

The top of the diaphragm has been built with specific thicknesses that lets the top be pushed, but not distort into the middle of the diaphragm. The sides of the face of the diaphragm were specifically built, in terms of their thickness, to be the "springs" that would help action the diaphragm to move back to its original shape once air returns through the dual purpose Duck-bill/Umbrella valve.

The thickness of the face, where the pressure is applied and the thinness of the sides of the face, acting as "springs," has been based on trial, error, and pressure analysis. An accordion or spring like action was also added to the border of the face of the reservoir to enhance the dynamic of the "pump-like" movements. The LDPE material of the reservoir is a perfect component material to achieve this dynamic of pressure millions of times over without breaking or distorting.

Reservoir Design

For injection molded parts, it made perfect stylish sense for the aesthetic to be a round diaphragm to appear similar to a watch on your wrist. The roundness of the diaphragm was also chosen for the ability to wear a WearSpray device without it looking odd, unfamiliar, or out of place on somebody's wrist.

Umbrella Valve Holes & Design

Trials and specific design measurements had to be made and special attention had to be paid to the size of the intake valves. As well, special attention to the positioning of the holes and their relationship in to the edges of umbrella valve. The valve holes had to be positioned around the "center ring," to be in the exact position to work with the secondary valve "umbrella." They are set in the gate or seat of the valve is such a way, to blow the umbrella valve back to let the air in, but also not leak.

This dual-purpose valve was also created with no glue or extension device, so that it could be assembled quickly and easily.

Gate Thickness

Due to the size of the reservoir, special attention also had to get paid to the actual gate thickness where the valves holes are. A valve gate that is too thick will not flex properly and work well with the dynamic of the size of the reservoir.

Three Components

Having all these elements work properly together, the reservoir can dispense over 90 streams of liquid fluid or gel in a minute. Each time that the stream passes through the duckbill, an opposite stream of air passes back through the valves holes, pushing back the umbrella valve to let the air back in.

This process re-purposes the diaphragm back to its original shape to begin the process again. The entire process must occur quickly, with no added assistance of springs or levers often seen in a spray bottle or other prior art.

Also, the WearSpray device works with no pressurized canisters, secondary pumps, levers, pistons or batteries.

A WearSpray Reservoir could also be made in the future with two different valves on either ends of the reservoir one dispensing fluids or lotions the other letting air back in. WearSpray's Clean bands is unique and can clearly be differentiated from its competitors. The reservoir was created with the intent to be refilled quickly and easily, without the need for a secondary needle-nose-device, often used by competitor wristbands.

Back Cap

Advantageously, the present invention has a watertight seal. In order to achieve the design of the airtight reservoir, we worked through various iterations of how a container is closed. An alternative would be to have a living hinge as the closure sealant for a WearSpray device.

Always trying to bring the components down to its simplest forms with as few working parts as possible, we discovered how other air tight devices close in the injection molded world of manufacturing.

The premise of an air-tight system snapping shut, is called an Annular Seal. An Annular Seal is normally seen in designs, used to snap shut a pen into its airtight cap. Normally Annular Seals work well due to their small size. We decided to incorporate this idea into WearSpray's design and creative processes. In doing so, we had to determine the larger angles and the flexing materials needed and how it would respond in the reservoir's rim.

The design and angles of the rim had to be airtight and created to snap into place. After many trials, we were able to angle the design of the walls of the annular seal mechanism precisely to create the seal and airtight lock of the reservoir. The cap can be easily pulled off to allow for a large refill area and then snapped back on to the reservoir without leaking any fluid. Other prior art it seems could not come to these conclusions and thus use a secondary needle nose device to refill through a very small hole or channel. The purpose of WearSpray is to be easily accessible, easy to refill and not to have any secondary devices that need to be carried around in case of the need for refilling.

Band Material

The band of the WearSpray wristband is made with a liquid silicone rubber that is biocompatible, comfortable, and durable. Due to the ability of transparent liquid silicone rubbers, various colorants can also be added to the Wear-Spray liquid silicone rubber for achieving stylish, modern colors for the bands.

Method of Use

A WearSpray device is refilled with an airtight cap that is opened and filled with a choice of liquid solution lotion or gel. A WearSpray device can be placed on the wrist or hung around the neck for the person to easily access the aforementioned solution.

Unlike all other known wristbands, special attention was also placed on the overall ease and ergonomics of the design, with the nozzle and valve facing away from the user.

This design allows the individual wearing the device, to simply raise the hand that the wristband is on and turn it down. In this way, the user can bring the adjacent palm to cup underneath and capture the fluid. In this configuration, the fingers of the adjacent hand, are in the perfect position to push on the face.

This action is quick and clean in dispensing directly into the other palm. This movement is also discreet and plays into the social norms of not being seen or noticed sanitizing, or sanitizing after shaking someone else's hand.

This design allows gravity to work, as the fluid naturally seeks the lowest part of the reservoir, when the wrist is turned down. The fluid travels to reach the nozzle/valve, thereby taking advantage of every drop of the reservoir fluid.

While a particular form of the invention has been illustrated and described, it will be apparent that various modifications can be made without departing from the spirit and scope of the invention. Accordingly, it is not intended that the invention be limited, except as by the appended claims.

Particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless the above Detailed Description section explicitly defines such terms. Accordingly, the actual scope of the invention encompasses not only the disclosed embodiments, but also all equivalent ways of practicing or implementing the invention.

The above detailed description of the embodiments of the invention is not intended to be exhaustive or to limit the invention to the precise form disclosed above or to the particular field of usage mentioned in this disclosure. While specific embodiments of, and examples for, the invention are described above for illustrative purposes, various equivalent modifications are possible within the scope of the invention, as those skilled in the relevant art will recognize. Also, the teachings of the invention provided herein can be applied to other systems, not necessarily the system described above. The elements and acts of the various embodiments described above can be combined to provide further embodiments.

All of the above patents and applications and other references, including any that may be listed in accompanying filing papers, are incorporated herein by reference. Aspects of the invention can be modified, if necessary, to employ the systems, functions, and concepts of the various references described above to provide yet further embodiments of the invention.

Changes can be made to the invention in light of the above "Detailed Description." While the above description details certain embodiments of the invention and describes the best mode contemplated, no matter how detailed the above appears in text, the invention can be practiced in many ways.

Therefore, implementation details may vary considerably while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated.

While certain aspects of the invention are presented below in certain claim forms, the inventor contemplates the various aspects of the invention in any number of claim forms. Accordingly, the inventor reserves the right to add additional claims after filing the application to pursue such additional claim forms for other aspects of the invention.

What is claimed is:

1. A device for wearing on a wrist of a person and dispensing a liquid, the device comprising:
    a wristband having a central mount and two opposing ends, each end having one part of a two-part mechanical fastener cooperative to secure the wristband around the person's wrist;
    a container fixed with the central mount of the wristband, the container having a top side with a resilient pump diaphragm, a side wall having an open portion fixed with a nozzle, and a bottom side at least partially openable to allow filling of the container with the liquid, the top side, the side wall, and the bottom side all defining an internal volume within the container;
    whereby with the wristband secured around the wrist of the person, the person can depress the resilient pump diaphragm to force the liquid out of the nozzle to dispense the liquid;
    wherein the nozzle is normally closed when the resilient pump diaphragm is not depressed, but, under pressure when the resilient pump diaphragm is depressed, the nozzle opens to allow dispensing of the liquid therethrough; and
    wherein the nozzle includes an umbrella valve integrally formed therewith, and wherein the open portion of the side wall of the container includes a central aperture through which the nozzle traverses and a plurality of air apertures spaced radially around the central aperture through which air is pulled into the internal volume of the container when the resilient pump diaphragm is released.

2. The device of claim 1 wherein the bottom side of the container includes a removable cap that is removable from the container to provide access to the internal volume for refilling the container with the liquid.

3. The device of claim 2 wherein the removable cap includes screw threads that engage cooperative screw threads of the side wall of the container.

4. The device of claim 1 wherein the resilient pump diaphragm is made with an elastomeric rubber material, whereby depressing the resilient pump diaphragm reduces the internal volume within the container to force the liquid through the nozzle.

5. The device of claim 2 wherein the container is removably attached with the central mount of the wristband, such that with the removable cap removed from the container, the container is free to slide out of the central mount of the wristband.

6. The device of claim 1 wherein the central mount of the wristband includes an opening cooperative with the nozzle of the container to allow the liquid to be dispensed through the opening of the wristband.

7. The device of claim 6 wherein the container and the central mount of the wristband are keyed so that the container only fits into the central mount of the wristband in one orientation wherein the nozzle is aligned with the opening in the wristband.

8. The device of claim 1 wherein the nozzle is oriented away from the user on his left wrist, such that with his right hand the user can depress the resilient pump diaphragm while cupping his right hand under the nozzle to receive the liquid in his right hand.

9. The device of claim 1 wherein the nozzle is oriented away from the user on his right wrist, such that with his left hand the user can depress the resilient pump diaphragm while cupping his left hand under the nozzle to receive the liquid in his left hand.

10. The device of claim 2 further including an auxiliary container mount, wherein the container can be removed from the wristband and inserted into the auxiliary container mount.

11. The device of claim 1 wherein at least a portion of the container is transparent, whereby the amount of liquid in the internal volume can be visually ascertained.

12. The device of claim 2 wherein the side wall of the container includes a rim and the removable cap includes a cooperative receiver that forms an annular seal with the rim, the receiver temporarily deforming when the rim is inserted therein to form a water-tight frictional-fit seal.

13. The device of claim 12 wherein the removable cap is tethered to the rim at a living hinge integrally formed with the cap and the container.

14. The device of claim 1 wherein the resilient pump diaphragm is made with a low density polyethylene.

15. A device for wearing on a wrist of a person and dispensing a liquid, the device comprising:
    a wristband having a central mount and two opposing ends, each end having one part of a two-part mechanical fastener cooperative to secure the wristband around the person's wrist;
    a container fixed with the central mount of the wristband, the container having a top side with a resilient pump diaphragm, a side wall having an open portion fixed with a nozzle, and a bottom side at least partially openable to allow filling of the container with the liquid, the top side, side wall, and bottom side all defining an internal volume within the container;
    whereby with the wristband secured around the wrist of the person, the person can depress the resilient pump diaphragm to force the liquid out of the nozzle to dispense the liquid;
    wherein the bottom side of the container includes a removable cap that is removable from the container to provide access to the internal volume for refilling the container with the liquid;
    wherein the side wall of the container includes a rim and the removable cap includes a cooperative receiver that forms an annular seal with the rim, the receiver temporarily deforming when the rim is inserted therein to form a water-tight frictional-fit seal.

16. The device of claim 15, wherein the removable cap is tethered to the rim at a living hinge integrally formed with the cap and the container.

* * * * *